United States Patent [19]
Eden et al.

[11] Patent Number: 5,932,639
[45] Date of Patent: Aug. 3, 1999

[54] MALTODEXTRIN-BASED ADHESIVES

[75] Inventors: James L. Eden, East Millstone; Yong-Cheng Shi, Neshanic Station, both of N.J.; Russell J. Nesiewicz, Orland Park, Ill.; Joseph Wieczorek, Jr., Flemington, N.J.

[73] Assignee: National Starch and Chemical Investment Holding Corporation

[21] Appl. No.: 08/841,555

[22] Filed: Apr. 30, 1997

Related U.S. Application Data

[63] Continuation-in-part of application No. 08/643,643, May 6, 1996, Pat. No. 5,688,845, and application No. 08/643,719, May 6, 1996.

[51] Int. Cl.⁶ .............................. C08L 3/02; C08B 31/00
[52] U.S. Cl. .................... 524/48; 536/123; 536/123.1; 435/95; 435/96; 156/336
[58] Field of Search .................... 536/123, 123.1; 524/48; 156/336; 435/95, 96

[56] References Cited

U.S. PATENT DOCUMENTS

| | | | |
|---|---|---|---|
| 2,609,326 | 9/1952 | Pigman et al. | 195/31 |
| 2,808,381 | 10/1957 | Stone | 260/17.4 |
| 2,850,468 | 9/1958 | Giggey | 260/17.4 |
| 3,200,091 | 8/1965 | Sederlund et al. | 260/8 |
| 3,560,343 | 2/1971 | Armbruster et al. | 195/31 |
| 3,644,126 | 2/1972 | Bodner | 99/142 |
| 3,663,369 | 5/1972 | Morehouse et al. | 195/31 |
| 3,734,819 | 5/1973 | Knutson | 161/254 |
| 3,849,194 | 11/1974 | Armbruster | 127/29 |
| 3,853,706 | 12/1974 | Armbruster | 195/31 R |
| 3,922,196 | 11/1975 | Leach et al. | 195/31 R |
| 3,922,197 | 11/1975 | Leach et al. | 195/31 R |
| 3,922,199 | 11/1975 | Hebeda et al. | 195/31 R |
| 3,954,687 | 5/1976 | Wiest et al. | 260/17 A |
| 4,014,743 | 3/1977 | Black | 193/31 R |
| 4,241,183 | 12/1980 | Witt et al. | 435/95 |
| 4,316,956 | 2/1982 | Lützen | 435/96 |
| 4,575,525 | 3/1986 | Wacome et al. | 524/48 |
| 4,643,894 | 2/1987 | Porter et al. | 424/35 |
| 4,678,824 | 7/1987 | Lauria | 524/48 |
| 4,725,441 | 2/1988 | Porter et al. | 424/479 |
| 4,828,841 | 5/1989 | Porter et al. | 424/479 |
| 4,921,795 | 5/1990 | Bozich, Jr. | 435/96 |
| 5,296,535 | 3/1994 | Nesiewicz et al. | 524/446 |
| 5,445,950 | 8/1995 | Kobayashi et al. | 435/99 |
| 5,532,300 | 7/1996 | Koubek et al. | 524/48 |
| 5,536,764 | 7/1996 | Nguyen et al. | 524/48 |
| 5,565,509 | 10/1996 | Nguyen et al. | 524/47 |
| 5,688,845 | 11/1997 | Eden et al. | 524/48 |

FOREIGN PATENT DOCUMENTS

| | | |
|---|---|---|
| 231729 | 8/1993 | European Pat. Off. . |
| 37 31 293 A1 | 4/1980 | Germany . |
| 46-14706 | 4/1971 | Japan . |
| 1406508 | 9/1975 | United Kingdom . |

*Primary Examiner*—Andrew E. C. Merriam
*Attorney, Agent, or Firm*—Margaret B. Kelley; Eugene Zagarella, Jr.

[57] ABSTRACT

The present invention is directed to remoistenable and non-remoistenable adhesives which contain at least about 50 wt % of a maltodextrin syrup having a reducing sugar content of about 5–19 dextrose equivalent and solids content of about 60–80 % water, and an effective amount of other conventional adhesive additives. When the adhesive is a remoistenable adhesive, a chemically derivatized starch having an amylose content of 40 % or less and a D.S. of about 0.01 to less than about 0.50 is used. A preferred remoistenable adhesive also contains polyvinyl acetate and/or ethylene vinyl acetate in an amount from about 15–90 wt. % The maltodextrin syrup is prepared from a converted or a non-converted, chemically derivatized or underivatized granular starch, by a high solids, single phase enzyme conversion process. When derivatized, the maltodextrin has (i) substituents in an amount sufficient to provide a degree of substitution between greater than about 0.01 and less than about 0.50. Some of the chemically-derivatized maltodextrins have a polymodal molecular weight distribution with one peak between about 630–1600 daltons and at least one other peak between about 1600–2,500,000 daltons.

16 Claims, No Drawings

MALTODEXTRIN-BASED ADHESIVES

This application is a continuation-in-part of application Ser. No. 08/643,643 filed May 6, 1996, now U.S. Pat. No. 5,688,845 and pending application Ser. No. 08/643,719 filed May 6, 1996.

BACKGROUND OF THE INVENTION

This invention relates to the use of unique high solids maltodextrin syrups in adhesives, particularly remoistenable adhesives such as envelope adhesives and non-remoistenable adhesives such as bookbinding adhesives.

Starches and dextrins have long been used as an adhesive material in various applications such as the fabrication of corrugated board, paper bags, paper boxes, laminated paperboard, spiral-wound tubes, gummed labels, gummed tapes and other gumming applications. See the discussion in Starch Chemistry and Technology, 2nd Edition, by R. Whistler et al., 1984, pp. 593–610 and Chapter 22 "Starch and Its Modifications" by M. W. Rutenberg, pp. 22–63 and 22–64 in "Handbook of Water-Soluble Gums and Resins" edited by Robert L. Davidson and published by McGraw-Hill Book Co. (1980).

Typical adhesive categories include liquid adhesives, pastes, cold-water-soluble adhesives, water-resistant adhesives, and numerous other applications. In most applications, the starch is cooked and solubilized and used as either the only component in addition to the water in the adhesive or as an added component in more complex formulations to provide the required tack, overall adhesion, solution viscosity, stability, and/or desired rheological characteristics.

Adhesives for specific applications include corrugating adhesives, multiwall bag adhesives, laminating adhesives, tube-winding adhesives, labelling adhesives, side bag seam adhesives, tissue and towel adhesives, cigarette adhesives, wallpaper adhesives, adhesives for disposables, remoistenable adhesives, bookbinding adhesives, cup and plate adhesives, case and carton seal adhesives, carton forming adhesives, glued lap adhesives, and the like.

Remoistenable adhesives are commonly utilized in the production of envelopes, stamps, wallpaper, tapes, labels and similar products where it is desired to provide a dry, but remoistenable, adhesive film. In the manufacture of remoistenable adhesives, typically an aqueous solution or dispersion or an organic solvent solution of the dry adhesive material is applied as a wet film to a substrate. After the water or organic solvent is removed by drying and evaporation, the resulting dry adhesive film will, on being moistened, produce the desired tacky adhesive surface.

The ability to provide an adhesive which is remoistenable is not in itself difficult and, in fact, there are a number of known and commercially available products that are used in various applications requiring remoistenable adhesives. Conventional remoistenable adhesives have generally been prepared from either of two adhesive systems. The first class includes adhesives prepared by the addition of dextrin, plasticizer, and other additives to dextrin-emulsified vinyl acetate homopolymers. The second class includes polyvinyl acetate homopolymers and copolymers which are emulsified with polyvinyl alcohol or dextrin to which additional polyvinyl alcohol or dextrin and plasticizer may be post-added.

The usefulness of a particular composition as a remoistenable adhesive in a specific application will depend on its ability to meet the many physical and chemical property requirements and to best satisfy the processing conditions to which it is subjected. Accordingly, a remoistenable adhesive composition in addition to providing good adhesion and remoistenability, typically is expected to provide a lay flat or non-curl product, be processable on different manufacturing equipment, provide adequate drying speed, resist hygroscopic and thermal blocking, and satisfy various other requirements depending on the application involved.

Remoistenable adhesives based on dextrins and/or modified starches now require a tradeoff in desirable properties such as adequate adhesion and tack, high solids content (60–70%), and stable useable final viscosity (2500–25,000 cps). Typically, a high molecular weight starch or dextrin is required for adhesion but a lower molecular weight starch or dextrin is required for viscosity and stability.

An adhesive is stable if it remains at a near constant viscosity after manufacture. Most adhesives are utilized within a year of manufacture. If the adhesive increases or decreases in viscosity over time, the machining characteristics will be adversely affected as well as the storage handling and/or shelf life. If the viscosity increases over time, pasting or non-flow will occur, the adhesives will no longer function properly and poor coating will result. Flow problems can also occur when the adhesive is removed from the storage containers which can range in size from 5 to 7000 gallons or more.

One method of "stabilizing" a starch- or dextrin-based adhesive is by heating the cooked dextrin or starch in the presence of formaldehyde or glyoxal to effect a light crosslinking which minimizes retrogradation of the starch or dextrin (i.e., loose hydrogen bonding), which is commonly referred to as "pasting".

An inherent problem exists because higher molecular weight dextrins provide excellent adhesion, but the adhesives are extremely high in viscosity and have poor viscosity stability, whereas lower viscosity adhesives contain excessive water (added to achieve acceptable machine viscosities) but, as a result, the overall adhesive solids are lowered. The use of low solid adhesives also results in slow machine speeds since the coated adhesive must be dried before packaging. In contrast, low molecular weight dextrins provide low viscosity, high solids adhesives which give poor adhesion and poor tack on remoistening.

Humidity resistance is very important when formulating a remoistenable adhesive. The adhesive should not be prematurely reactive when exposed to normal atmospheric conditions.

"Blocking" is the undesirable adhesion that can occur between touching layers of a material under certain conditions. Hygroscopic blocking resistance is the ability of the adhesive to resist reactivating due to humidity. In a situation where substrates, such as envelopes or sheets of stamps, are coated with an adhesive which is non-resistant to hygroscopic blocking and are stored and exposed to varying degrees of humidity, there is a tendency for adjacent surfaces of the stacked substrates to adhere and stick to one another. Thermoplastic blocking is the adhesion that can occur when adhesive coated substrates are exposed to varying temperatures and pressures during processing, storage and other handling operations. Pressure conditions causing blocking can exist, for example, during storage or stacking of products while processing, during the printing of products such as the laser jet printing of papers and envelopes, and during the perforating of sheets of stamps and other products. Depending on the particular conditions used, the amount of pressure that is created can cause blocking in non-resistant adhesive formulations.

Hygroscopic blocking has been more particularly defined by a standard test method, ASTM D 114653. Hygroscopic blocking is measured on a test specimen at 50 percent relative humidity at 38° C. for 24 hours. If there is no blocking (free), it is then measured at increments of successively higher humidities until blocking occurs (critical humidity) or until a suitably high humidity is reached. Thermoplastic blocking is measured under the same. ASTM D procedure at 38° C. for 24 hours. If there is no blocking (free), it is measured at successively higher temperatures (increments of 5° C.) until blocking occurs (critical temperature) or until a suitably high temperature is reached. Especially suitable high humidity and high temperature conditions for determining hygroscopic and thermoplastic blocking are 95 percent relative humidity and 90° C.

Since remoistenable adhesives are mainly used on paper substrates, the use of excessive water can also result in poor lay-flat or "curling" of the coated surface. The paper absorbs water and swells, distorting the original configuration of the paper fibers. As the adhesive dries, wrinkling or "curling" occurs due to the unequal rates of expansion and contraction of the paper backing and adhesive film.

Excessive curl can cause equipment jam-ups or other handling difficulties. While some adhesive materials have good lay flat or non-curl properties, others require various techniques such as the addition of humectants to overcome or minimize this curling tendency. While these techniques often alleviate the curling problem, other properties such as hygroscopic blocking resistance can be unfavorably affected.

To solve this problem, one can reduce the overall amount of water in the final adhesive formulation or add humectants which act as diluents and do not distort the paper fibers. The use of humectants, however, increases the time required to dry the adhesive. The use of humectants also reduces the adhesive's humidity resistance since the humectants are hygroscopic.

Pyrodextrins are used in the preparation of many liquid and dry adhesives including remoistenable adhesives. There are four major steps in the manufacture of pyrodextrins: acidification, predrying, dextrinization, and cooling. In the early stages, hydrolysis is the major reaction and the viscosity of the starch is substantially reduced to near the level of the finished dextrin. Repolymerization becomes a major factor as the temperature rises. As the reaction progresses, an equilibrium viscosity is approached, and at increasing temperatures, a transglucosidation reaction predominates. There are two major characteristic changes—one is the molecular size of the dextrin molecule, the other is a change in the degree of linearity. Each has a specific effect on the physical and chemical characteristics of the dextrin. Variation in average molecular weight influences the dextrin's viscosity, while changes in linearity greatly influence the solution stability.

The use of pyrodextrins in remoistenable adhesives requires compromises in adhesive formulating between the desired solids, viscosity, tack/strength and stability. In addition, the adhesives suffer from color problems.

Bookbinding adhesives require superior adhesion and various classes of adhesives are utilized in the bookbinding industry. For example, synthetic emulsion adhesives, such as polyvinyl alcohol or ethylene vinyl acetate emulsion polymers, are used on endpapers, for tipping, for gluing-off operations, for lining, casing-in, spine gluing and side gluing, and on special stencil applicator case makers. Hot melt adhesives, which consist of polymers, tackifier resins and waxes, are used mainly as one-shot adhesives for pocket-books and magazines, in multi-shot applications in the production of catalogues, and in burst binding. Starches derived from maize, potato, and tapioca are used for producing pastes, generally for the hand-binding section of the trade and sometimes for operations such as endpapering and tipping or for hand case making in leather.

Case making is one of the more demanding bookbinding techniques. Because of the adhesive properties required, animal glues are mainly used for case making and lining and only occasionally in unsewn binding lines. Animal glues consist of one or more kinds of gelatine in a solution of water. They give aggressive tack with a medium-set speed. Since they are derived from natural materials, they are very susceptible to seasonal factors and tend to vary with their source of supply. Operators using these glues have to be skilled in achieving the correct degree of dilution and tack. Most animal glues age and become brittle under dry, warm conditions as evidenced by the condition of the spine of a book kept for some time in a centrally heated home.

Most cigarette making adhesives are based on synthetic polymer systems. There is, however, a growing trend to the use of natural products in this area. Modified starches, such as chemically modified starches and dextrins, are being used for such constructions. Adhesives containing these starches and dextrins have a Brookfield viscosity of approximately 500–5000 cps., and they are used in all applications including side seams and tipping. A side seam is the bond produced to facilitate the formation of the tobacco filled cigarette rod. Tipping is the process by which the separate filter section is combined with the tobacco filled section by means of an overlapping bond.

Corrugating adhesives are prepared using starch, water, alkali, and other optional ingredients, e.g., a waterproofing agent. Starches used as the carrier portion may contain portions or mixtures of high amylose starch.

There is a need for improved maltodextrin-based adhesives having a high adhesive solids content, which maintain a useable viscosity during storage, and which provide good adhesion and which also provide good lay flat properties, block resistance, and tack when the adhesive is a remoistenable adhesive and resistance to humidity changes when the adhesive is a bookbinding adhesive.

SUMMARY OF THE INVENTION

The present invention is directed to adhesives containing unique maltodextrin syrups which are prepared by a novel high solids, enzyme conversion process. The adhesives include high solids, maltodextrin-based remoistenable adhesives, resin-based remoistenable adhesives, and non-remoistenable adhesives. As used herein, "remoistenable adhesives" include liquid or paste adhesives which are coated onto substrate(s), dried, later reactivated, by heat and/or moisture and then bonded to another uncoated or coated substrate. As used herein, "non-remoistenable adhesives" include liquid or paste adhesives which are coated on one or more substrates which are wet combined and then dried to form the bond.

The high solids, remoistenable adhesives consist essentially of:
a) at least about 50% by weight of a maltodextrin syrup having a solids content between about 60 to 80% by weight and a water content of about 40 to about 20% by weight, which is prepared from a converted or a non-converted, chemically derivatized starch having an amylose content of 40% or less; which maltodextrin has (i) substituents in an amount sufficient to provide a degree of substitution of greater than about 0.01 and less than about 0.50; (ii) a reducing sugar content of between about 5 and about 19 dextrose equivalent; and (iii) a polymodal molecular weight distribution having one peak between about 630 to about 1600 daltons and at least one other peak between about 1600 and about 2,500,000 daltons;

b) 0 to about 50% by weight of water; and c) an effective amount, based on the weight of the maltodextrin syrup in the remoistenable adhesive, of a preservative, a humectant, a defoamer, a plasticizer, and/or a peptizing salt. The high solids, remoistenable adhesive described above preferably will have a maltodextrin syrup content of from about 70% to less than 100% by weight and more preferably about 70 to about 90%. The reducing sugar content of the maltodextrin preferably will be between about 10 and about 17 dextrose equivalents. The substituents in the maltodextrin will preferably be in an amount or degree of substitution of between about 0.05 and less than about 0.17.

The resin-based remoistenable adhesives consist essentially of:

a) about 15 to about 90% by weight of a resin selected from the group consisting of polyvinyl acetate, ethylene vinyl acetate, and mixtures thereof;

b) about 10 to about 85% by weight of a maltodextrin syrup having a solids content between about 60 to about 80% by weight and a water content about 40 to about 20% by weight, which is prepared from a converted or a non-converted, chemically derivatized starch having an amylose content of 40% or less; which maltodextrin has (i) substituents in an amount sufficient to provide a degree of substitution of greater than about 0.01 and less than about 0.50, (ii) a reducing sugar content of between about 5 and about 19 dextrose equivalent, and a polymodal molecular weight distribution having one peak between about 630 to about 1600 daltons and at least one other peak between about 1600 and about 2,500,000 daltons; and c) 0 to about 75% by weight of water.

When the remoistenable adhesive is the resin-based adhesive, the polyvinyl acetate and/or ethylene vinyl acetate may be emulsified during polymerization of the monomers with part of the maltodextrin syrup which acts as a protective colloid. The amount of maltodextrin syrup used as the protective colloid is about 25% of the wet emulsion. Partially hydrolyzed, moderate molecular weight polyvinyl alcohol may be added to the adhesive in addition to, or as a partial replacement for, the polyvinyl acetate or polyethylene vinyl acetate resins in an amount of up to 10%, more preferably 2–5%, of the wet formula. A suitable polyvinyl alcohol is Airvol 203 from Air Products, Allentown, Pa.

The remoistenable adhesives are characterized by their combination of dry strength, wet tack, remoistenability, long term viscosity stability, and light color in comparison to remoistenable adhesives formulated with pyrodextrins. In addition, clay or other lay-flat additives may not be required.

The non-remoistenable adhesives consist essentially of:

a) at least about 50% by weight of a maltodextrin syrup having a solids content between about 60 to 80% by weight and a water content of about 40% to about 20% by weight and which is prepared from a converted or a non-converted starch and which has a reducing sugar content of between about 5 and about 19 dextrose equivalent;

b) 0 to about 50% by weight of water; and c) an effective amount, based on the weight of the maltodextrin syrup in the non-remoistenable adhesive, of a preservative, a humectant, a defoamer, a plasticizer, and/or a peptizing salt. Preferably, the maltodextrin syrup content in the non-remoistenable adhesives described above will be about 70% by weight. The reducing sugar content of the maltodextrine preferably will be between about 10 and about 17 dextrose equivalents. The maltodextrin syrup in the non-remoistenable adhesive may also be a chemically derivatized starch as described above for the remoistenable adhesive containing different substituents such as non-ionic, anionic or cationic ether and/or ester substituents. Preferably the substituent groups will be in an amount or degree of substitution between about 0.05 and about 0.17.

The non-remoistenable adhesives are characterized by their combination of dry strength, long term viscosity stability, and light color in comparison to non-remoistenable adhesives formulated with pyrodextrins.

The adhesives may be prepared from a powdered maltodextrin recovered by drying the maltodextrin syrup and then adding water or the aqueous based resin. The non-remoistenable adhesives may also be prepared from the powdered maltodextrin by adding water or a suitable solvent.

Preferably, the maltodextrins are prepared by a single phase, high solids enzyme conversion which provides maltodextrins with a unique polymodal molecular weight profile, when the starch is a derivatized starch. This "polymodal" profile is advantageous for the claimed adhesives because the higher molecular weight portions of the maltodextrin syrup provide the required adhesion, while the lower molecular weight portions of the maltodextrin syrup provide lower final viscosities. Previously, these characteristics could only be achieved by blending different starches and/or dextrins. The chemically derivatized maltodextrins produced in the single phase process are inherently stable and no glyoxal or formaldehyde stabilization is required.

In the single phase process for preparing the chemically derivatized maltodextrins, a portion of the starch can be unaffected by the enzyme conversion. The ungelatinized or partially gelatinized granules (generally less than 1%) alter film continuity and contraction and thus contribute to the remoistenable adhesive's lay-flat properties and humidity resistance. The resultant improvement in the remoistenable adhesive's non-curl or lay-flat properties results in a reduction in the use of humectants, which in turn results in faster application speeds and faster drying times.

The single phase, high solids enzyme conversion process involves the steps of:

(a) adding, to a converted or unconverted, chemically derivatized or a non-derivatized granular starch, water and a starch-hydrolyzing enzyme, the water being used in an amount sufficient to produce a single phase powdered mixture without a visible free water phase;

(b) activating the enzyme by heating the powdered mixture to about the optimum temperature for the enzyme while maintaining a substantially constant moisture content (i.e., within ±5% from the starting moisture content) in the mixture;

(c) allowing the enzyme to hydrolyze and liquefy the starch; and (d) optionally inactivating the enzyme by reducing the pH, increasing the temperature, and/or adding an inhibiting salt.

As used herein, "starch" is intended to include non-pregelatinized granular starches, pregelatinized granular starches, and starches which are pregelatinized but not cold-water-soluble and the chemically derivatized starches contain ether and/or ester non-ionic, anionic, or cationic substituent groups. Preferred ether groups are hydroxypropyl, 3-(trimethyl ammonium)-2-hydroxypropyl, or N,N-diethylaminoethyl groups. Preferred ester substituent groups include succinate, octenylsuccinate, acetate or phosphate groups.

As used herein, "single phase" means a mixture which has no visible free water, whereas a "slurry" consists of two phases, i.e., a water phase and a starch phase. The preferred total water content of the conversion process is about 15 to 40% by weight of the total mixture, except when a converted granular starch is being prepared with only alpha amylase where the total water content is about 15–35%.

The powdered or preferably liquid enzyme and sufficient water to give the desired total moisture content are dispersed onto a granular starch powder. The typical moisture content of granular starches is about 10–14%. Thus, sufficient water is added in step (a) to bring the total amount of water to the desired amount. As used herein, the term "total amount of water" refers to the total of the equilibrium moisture typically present in a granular starch and the added water.

If the moist single phase powdered mixture is subjected to a mixing process which kneads and compacts, such as that typical of dough mixing equipment or viscous polymer compounding equipment, it may, depending upon the water content and amount of solubles present, become a very high viscosity compact doughy mass before the onset of gelatinization and conversion. Continued mechanical shearing will raise the temperature and cause gelatinization and conversion.

When the powdered mixture starch contains a granular starch, as the powdered mixture is heated, the heat and moisture initiate the swelling of the starch granules and the starch is completely or partially gelatinized and simultaneously converted. When the powdered mixture contains a pregelatinized, non-cold-water-dispersible starch, the heat and moisture disperse the starch and the starch is fully gelatinized and simultaneously converted. As the starch is converted, usually the powder liquefies. The peak viscosity of the native starch is never reached.

The maltodextrin may be in the form of a syrup, a converted granular starch, or a mixture of the syrup and the converted granular starch. As used herein, "syrup" covers liquids and viscous pastes. The resulting starch syrup is obtained at a high solids content (e.g., at least 60%, typically 65–75% by weight). The syrup may be spray dried, belt-dried, or freeze dried. The enzyme-converted starch may be recovered from the starch syrup as a water-soluble powder. If desired, the sugar by-products may be removed from the granular converted starch by washing.

The enzyme may be activated by direct or indirect heating and/or pH adjustment to the optimum temperature and pH for the particular enzyme used. Optionally, an enzyme activator such as certain inorganic salts and/or a pH adjuster such as an acid, a base, or a buffer may be used. The enzyme may be inactivated by adjusting the pH, adding an inhibiting salt, or increasing the temperature.

The water content during the conversion is affected by the product solids, the condensation of injected steam used for direct heating, and evaporation during the conversion. The product solids are increased by the hydrolysis. During conversion to a D.E. of 100, the dry weight of the starch is increased by 11.11% due to water covalently bound to the hydrolysis reaction products. This dry weight increase is proportional to the degree of conversion. The solids are decreased due to the condensed steam and increased by evaporation.

The powdered mixture of the starch, water, and enzyme does not require stirring during the enzyme conversion step. In contrast to prior art enzyme conversion processes, the process is carried out at such a high solids content that the mixture is a single phase.

DESCRIPTION OF THE PREFERRED EMBODIMENTS

Suitable starches depend on whether or not the adhesive is a remoistenable adhesive. Suitable starches for the remoistenable adhesives include any starches having an amylose content of less than 40%. Any starch is suitable for the non-remoistenable adhesives, including high amylose starches, (i.e., starches having an amylose content of 40% or above). The starch can be derived from any source. Typical sources for the starches are cereals, tubers, roots, legumes, fruit starches, and hybrid starches. Suitable native sources include corn, pea, potato, sweet potato, wheat, rice, sorghum, waxy starches such as waxy maize, waxy tapioca, waxy rice, waxy barley, waxy wheat, waxy potato, waxy sorghum, and the like. A "native" starch is an unmodified starch. It may be possible to convert flours provided effective enzyme levels are used to obtain sufficient conversion.

The use of humectants in remoistenable adhesives may cause, or can contribute to, hygroscopic blocking. In non-remoistenable adhesives salts are often used at relatively high levels, with the amount used being adjusted to lower levels when the adhesive is used in a humid environment.

Chemically derivatizing the starch can lower the gelatinization temperature and make it easier to carry out the conversion. The chemical modifications useful herein include heat- and/or acid-conversion, oxidation, phosphorylation, etherification, esterification, crosslinking, and conventional enzyme modification. These modifications are preferably performed before the starch is enzyme converted. Procedures for chemically modifying starches are described in the chapter "Starch and Its Modification" by M. W. Rutenberg, pages 22–26 to 22–47, Handbook of Water Soluble Gums and Resins, R. L. Davidson, Editor (McGraw-Hill, Inc., New York, N.Y. 1980). Since high amylose starches are harder to gelatinize, it will also be necessary to use a higher level of chemical substitution to lower the starch's gelatinization temperature. The increased substitution, however, inhibits the enzyme conversion.

The degree of substitution (D.S.) is an indication of the amount of chemical substitution of the hydroxyl groups of a glucose unit. Each glucose unit has three reaction sites and a D.S. of 1 indicates that one site has reacted. The chemical substituents interfere with and stop the enzyme conversion so that fully converted products are not obtained. The more highly substituted the starting starch material, the higher the molecular weight of the maltodextrin as there is less enzyme conversion.

Granular starches which have not been pregelatinized are preferred. Granular pregelatinized starches are also useful herein. The pregelatinized granular starches are prepared by processes known in the art. The pregelatinization is carried out in such a way that a majority of the starch granules are swollen, but remain intact. Exemplary processes for preparing pregelatinized granular starches are disclosed in U.S. Pat. No. 4.280.851, U.S. Pat. No. 4.465.702, U.S. Pat. No. 5.037.929, and U.S. Pat. No. 5.149.799, the disclosures of which are incorporated herein by reference. Predispersed (i.e., pregelatinized starches) can also be used in the high solids, single phase enzyme conversion process provided they are not cold-water-soluble. They can be prepared by jet-cooking and spray-drying.

Physically modified starches, such as the thermally-inhibited starches described in WO 95/04082 (published Feb. 9, 1995), are also suitable for use herein provided they have also been chemically modified.

Suitable enzymes for use herein include bacterial, fungal, plant, and animal enzymes such as endo-alpha-amylases which cleave the 1→4 glucosidic linkages of starch, beta amylases which remove maltose units in a stepwise fashion from the non-reducing ends of the alpha-1,4-linkages, glucoamylases which remove glucose units in a stepwise manner from the non-reducing end of the starch molecules and cleave both the 1→4 and the 1→6 linkages, and debranching enzymes such as isoamylase and pullulanase which cleave the 1→6 glucosidic linkages of amylopectin-containing starches. Alpha amylases or mixtures thereof with other enzymes are preferred and are used for preparing the enzyme-converted starches having unique bimodal or polymodal molecular weight profiles.

Enzymes can be purified by selective absorption or precipitation, but many commercial products contain significant amounts of impurities in the form of other enzymes, as well as in the form of inert proteins. For example, commercial bacterial "amylases" will sometimes also contain "proteinases" (enzymes which break down protein). After extraction and partial purification, commercial enzymes are sold either as powders or as liquid concentrates.

Process conditions for the use of a particular enzyme will vary and will usually be suggested by the supplier. The variables include temperature, pH, substrate solids concentration, enzyme dose, reaction time, and the presence of activators. Very often there are no absolute optimum reaction conditions. The "optimum" pH may depend on temperature; the "optimum" temperature may depend on reaction time; the "optimum" reaction time may depend on cost, and so on. The reaction time can vary from 10 minutes to 24 hours or more, typically 1 to 4 hours for alpha amylase. The recommended conditions therefore are usually compromises.

The stability of an enzyme to adverse conditions is usually improved by the presence of its substrate. Some enzymes are also stabilized by certain salts (bacterial amylase is stabilized by calcium salts). It is necessary to rigorously exclude heavy metals and other enzyme poisons, such as oxidizing agents, from an enzyme reaction since these materials usually result in permanent inactivation (i.e., denaturization) of the enzyme. There are many instances however where enzyme activity is reduced reversibly, frequently by the products of a reaction (product inhibition) or by a substance which is structurally related to the usual substrate (competitive inhibition). Reversible inhibitors complex temporarily with the enzyme and therefore reduce the amount of enzyme available for the normal reaction. Typical enzyme reaction conditions are discussed in "Technology of Corn Wet Milling" by P. H. Blanchard, Industrial Chemistry Library, Vol. 4 (Elsevier, New York, N.Y. 1992).

The optional humectants used herein may be any of those conventionally used in formulating adhesives. Typical humectants include sugars, sorbitol, glycerin and related derivatives, propylene glycol and similar related glycols, and glycol ethers. These humectants are used in the remoistenable adhesive formulations at levels of about 0.5 to 10% by weight of the total adhesive formulation.

A minor amount of polyvinyl alcohol (about 0.05 to about 4% by weight) may be added to the remoistenable adhesives as a protective colloid. The polyvinyl alcohol can be a partially or a fully hydrolyzed polyvinyl alcohol. A suitable polyvinyl alcohol is Airvol 203 (available from Air Products, Allentown, Pa.).

In preparing the preferred remoistenable adhesive compositions, the maltodextrin syrup may be prepared and added to the ethylene vinyl acetate latex and/or polyvinyl acetate latex or a dry maltodextrin (recovered from the maltodextrin syrup by spray-drying or like drying methods) may be added directly to the latex. The maltodextrin may also be added during the monomer polymerization to act as a protective colloid.

In preparing the non-remoistenable adhesive composition, the maltodextrin syrup may be used directly or diluted to the desired solids or a dry maltodextrin syrup (recovered as discussed above) may be dispersed in water, in solvents such as alcohols, (e.g., propanol), esters (e.g. ethylacetate), or cycloalkenes (e.g., kylene), or in a water-based resin.

The adhesive composition is then heated and maintained at a temperature of about 71–82° C. (160–180° F.) with agitation for a period sufficient to ensure compete dissolution if the dry maltodextrin is used. Any other additives which are to be employed should be added at this point. The resulting mixture is then diluted with additional water, if necessary, to the desired viscosity, generally in the range of about 2,000 to 30,000 cps, preferably 2,000 to 20,000, most preferably about 6,000 cps for remoistenable adhesives. Depending the particular end use for the non-remoistenable adhesives the viscosity can vary from 500 to 200,000 cps. In the embodiment wherein maltodextrin syrup or powder is not post-added to the preferred resin-based remoistenable adhesives, it may be necessary to add a thickener (e.g., polyacrylamide, carboxymethyl cellulose, hydroxyethylcellulose, etc.) in order to obtain a: viscosity within these limits. In the final preferred remoistenable adhesive compositions, the maltodextrin syrup will be present in an amount of from about 10 to 85%, preferably from 50%, by weight of the formulation, with the ethylene vinyl acetate and/or polyvinyl acetate resin (optionally emulsified with the maltodextrin) comprising about 15% to about 40%, and with the remainder being water.

Various optional additives, such as humectants, defoamers, plasticizers, preservatives, thickeners, bleaching agents, peptizing salts such as magnesium chloride and sodium nitrate may also be present in the adhesive compositions in order to modify certain characteristics thereof, as long as they do not detrimentally affect the adhesion or the hygroscopic and thermoplastic blocking properties when the adhesive is a remoistenable adhesive. Such ingredients will generally be used in effective amounts of 5% by weight or less, typically in minor amounts of less than about 3% by weight for remoistenable adhesives. Such ingredients will generally be used in effective amounts of 30% by weight or less. A suitable defoamer is Foamaster III (available from Henkel Chemical Co.) in an amount of about 0.01–1%. A suitable preservative is Kathon in an amount of about 0.01–0.5%. A suitable plasticizer is a dibenzoate in an amount of about 0.5–5% %.

Although the optional additional maltodextrin has been referred to as being "post-added", it should be recognized that the post-addition is merely the most convenient and generally accepted method of formulating remoistenable adhesives, such as envelope adhesives, and that it is possible to add the additional maltodextrin directly to the monomer charge prior to the actual polymerization.

Remoistenable adhesives in which the high solids maltodextrins are useful include envelope adhesives and stamp gumming adhesives. Non-remoistenable adhesives in which the high solids maltodextrins are useful include book casing adhesives, laminating adhesives, tube core winding adhesives, case and carton adhesives, seam adhesives for grocery bags, envelopes and the like, corrugating adhesives, cigarette making adhesives, etc.

Test Procedures

Dextrose Equivalent

The dextrose equivalent (D.E.) is an indication of the degree of conversion as shown by the reducing sugar content of the maltodextrin.

A Fehling Volumetric Method, as adapted from the Eynon-Lane Volumetric Method #423 of the Cane Sugar Handbook by Spencer and Mead (John Wiley and Son Inc.), is used to determine the D.E.

A starch solution (w/v) of known concentration on an anhydrous starch basis is prepared. The usual concentration is 10 g/200 ml. The starch solution is transferred to a 50 ml. burette. To 50 ml of distilled water in a 500 ml Erlenmeyer flask are added by pipette 5 ml each of Fehling Solutions A and B. Fehling Solution A contains 34.6 g of copper sulfate ($CuSO_4.5H_2O$) dissolved in and brought to volume in a 500 ml volumetric flask. Fehling Solution B contains 173 g of Rochelle salt ($NaKC_4H_4O_6.4H_2O$) and 50 g of sodium hydroxide dissolved in and brought to volume in a 500 ml volumetric flask. The Fehling Solutions are standardized against Standardized Dextrose obtained from the Bureau of Standards.

To determine the Fehling Factor, the test procedure is followed except that 0.5000 anhydrous grams of dextrose per 200 ml of distilled water is used as the test solution. Using the following formula the factor is then computed:

$$Factor = \frac{100 \times ml \text{ used in titration} \times g \text{ dextrose/ml}}{100}$$

The factor applies to both Fehling solutions A and B and is computed to 4 decimal places. The contents of the flask are brought to a boil over a hot plate. The starch solution, while at a boil, is titrated to the distinctive reddish-brown colored end point (precipitated cuprous oxide complex). The ml. of starch solution required recorded.

The Dextrose Equivalent (D.E.) is calculated using the following formula:

$$\% DE = \frac{(Fehling\ Factor) \times 100}{(g/ml\ starch\ concentration \times ml\ starch\ solution)},$$

where "starch solution" equals the ml of starch solution used in the titration to reach the end point and "starch concentration" equals the concentration of the starch solution on an anhydrous basis expressed in g/ml.

Gel Permeation Chromatography (GPC)

Molecular weight (MW) distribution is determined using a Water Associates GPC-150C Model with a refractive index (RI) detector. Two PL gel columns ($10^5$ and $10^3$ obtained from Polymer Laboratories of Amherst, Mass.) made of highly crosslinked spherical polystyrene/divinylbenzene, are connected in sequence. Dextrans from American Polymer Standards Corp. (Mentor, Ohio) are used as the standards. The experimental conditions are a column temperature of 80° C. and a flow rate of 1 ml/min. The mobile phase is dimethyl sulfoxide (DMS) with 5 mM of sodium nitrate ($NaNO_3$). The sample concentration is 0.1%. The injection volume is 150 µl.

Brookfield Viscometer

Test samples are measured using a Model RVT Brookfield Viscometer and the appropriate spindle which is selected based on the anticipated viscosity of the material. The test sample is placed in position and the spindle is lowered into the sample to the appropriate height. The viscometer is turned on and the spindle is rotated at a constant speed (e.g., 10 or 20 rpm) for at least 3 revolutions before a reading is taken. Using the appropriate conversion factors, the viscosity (in centipoises) of the sample is recorded.

Solids Content

The solids content of the adhesive is determined by oven drying the adhesive at 100–110° C. to a constant weight. Using the following formula the % solids are calculated:

$$\frac{Adhesive\ Weight\ Dry}{Adhesive\ Weight\ Wet} \times 100 = \% \ Solids$$

Setting Speed

Setting speed is the time it takes an adhesive to form a fiber-tearing bond which is achieved as a result of wet tack development. A faster setting adhesive allows a user to run the lines faster, accommodates short and low pressure compression zones, and produces a fiber tearing bond off-line insuring product performance. Set speed is very dependent on coat weight, compression, temperature and humidity. Therefore, comparisons should be made using the same application method and substrate under the same temperature and humidity conditions.

To test the set speed, two 15 inch long by 6 inch wide sheets of 50# brown Kraft paper are cut. Then cuts one inch wide and five inches long are made in one of the 15 inch pieces of the Kraft paper creating a "hula skirt". A glass plate, longer and wider than paper stock, is placed onto a clipboard and oriented horizontally with the clip to the left. The cut "hula skirt" Kraft paper is placed on the top of the other piece of Kraft paper and both are clipped to the clipboard-glass set up. The "hula skirt" is then folded up and back to expose the second sheet of Kraft paper. A piece of scrap paper is placed underneath and to the far right of the Kraft paper to catch excess adhesive when the drawdown is made. A bird applicator is centered to the far left on top of the bottom piece of Kraft paper. Four to six grams of adhesive are placed in the opening of the applicator. The adhesive is drawn down across the paper using even pressure. Excess adhesive is caught by the scrap paper. The "hula skirt" is over the top of adhesive film and is unfolded. A timer is immediately started as well as immediately hand rolling the adhesive to compress bond. Slowly the one inch sections are pulled up and the time when each section is pulled up is noted. The amount of fiber tear at each time interval is examined. The time at which consistent 50% or more fiber tear is acquired is noted. The set speed of the adhesive is the first time 50% or more fiber tear is achieved.

Open Time

Open time is the amount of time an adhesive film on one substrate may remain open (i.e., uncovered) and still form a durable bond when combined with a second substrate. An adhesive with a longer open time will tend to machine better. In other words, it will remain "wet" in the glue pot, on rollers and on stencil pads, and therefore be less likely to build up and form skins. Open time is very dependent on coat weight, temperature and humidity. Hence, when comparing adhesives, the same application method and substrates should be used at the same temperature and humidity.

The test is carried out using the above procedure for testing the set except that one of the two pieces of Kraft paper is cut into one inch strips and the strips are bonded to the Kraft paper coated with the adhesive film over consistent time intervals using the same pressure to compress the straps. The time that each strip is bonded is noted. A minimum of one hour is allowed for drying. Then, starting at the left side of the Kraft paper, the one inch strips are carefully peeled off and the strength and degree of fiber tear are noted. The open time is the first point where 50% or less fiber tear is noted. It may be necessary to repeat the test if the last strip has more than 50% fiber tear and begin bonding at a later time.

Lamination Test Procedure:

The adhesive composition is heated to 65° C. A glass plate is placed under the clip of a clipboard. A sheet of board stock is placed between the clip and the glass plate. Strips of cover stock are cut to dimensions of 3.5 inches long, 1.5 inches wide in the machine direction. A strip of cover stock is placed between the clip and the board stock such that the clip is positioned about 0.25 inches from the top of the cover stock strip. The remainder of the cover stock is folded back to expose the board stock positioned under the cover stock. A 1.5 mil bird applicator with a one inch gate (available from MCD Industries, Medfield, Mass.) is placed between the cover stock and the board stock. A bead of the heated adhesive is applied under the bird applicator and drawn down the board stock. The cover stock is contacted with the board stock immediately and rolled once with a roller to adhere the cover stock to the board stock. The adhesion of the cover stock to the board stock is evaluated the day after the draw downs by pulling the stock from the board and evaluating the condition of the bond. The percentage of bond surface showing fiber tear is recorded.

EXAMPLES

In the examples which follow, non-pregelatinized granular starches were used unless it is otherwise stated and the various enzymes described hereafter were used.

The alpha amylases were Ban 120 L and Termamyl. They were obtained from Novo Nordisk. Ban is a conventional alpha amylase with an optimum temperature of approximately 70° C., optimum pH of 6.0–6.5, an activity of 120 KNU/g, and recommended usage (based on the weight of the starch) of 0.005–1.0, preferably 0.01–0.5. Termamyl is a heat-stable alpha amylase with an optimum temperature greater than 90° C., an activity of 120 KNU/g, and recommended usage (based on the weight of the starch) of 0.005–1.0, preferably 0.01–0.5. One Kilo Novo unit (1 KNU) is the amount of enzyme which breaks down 5.26 g of starch (Merck, Amylum Solubile, Erg. B6, Batch 994 7275) per hour in Novo Nordisk's standard. Method for determining alpha amylase using soluble starch as the substrate, 0.0043 M calcium content in solvent, 7–20 minutes at 37° C. and pH 5.6.

The mixture of alpha amylase and glucoamylase used was Aspk 27 obtained Daikin Kogyo, Kabushigi, Kaisha, Osaka, Shi Kibanoku, Ichome 12–39 Japan. The optimum conditions are not disclosed.

The barley beta amylase used was Spezyme BBA 1500 which was obtained from Finnsugar Group. The optimum conditions for this enzyme are pH 5.0–7.0 and a temperature of 55–65° C. It has an activity of 1500 Dp°/ml and its recommended usage (based on the weight of the starch) is 0.1–2.0%, preferably 0.2–0.8%. One Degree of Diastatic Power (Dp°) is the amount of enzyme contained in 0.1 ml of a 5% solution of the sample enzyme preparation that produces sufficient reducing sugars to reduce 5 ml of Fehling Solution when the sample is incubated with 100 ml of substrate for 1 hour at 20° C.

Amyloglucosidase (AMG 300L) is an exo-1,4-alpha-D-glucosidase. Optimum conditions are pH 4.5 and 60° C. It has an activity of 300 AGU/ml recommended usage (based on the weight of the starch) of 0.005–1.0%, preferably 0.01–0.5%. One Novo Anhydroglucosidase Unit (AGU) is defined as the amount of enzyme which hydrolyzes 1 micro-mol of maltose per minute using maltose as the substrate at 25° C., pH 4.3 for 30 minutes.

The debranching enzyme used is Promozyme 600L (pullulanase) which was also obtained from Novo Nordisk. It is a heat-stable debranching enzyme with an optimum temperature of 60° C. and optimum pH of 5.2. It has an activity of 200 PUN/g and the recommended usage (based on the weight of the starch) is 1–15%, preferably 2–10% PUN/g. One Pullulanase Unit Novo (PUN) is defined as the amount of enzyme which under standard conditions hydrolyzes pullulan, liberating reducing carbohydrate with reducing power equivalent to 1 micro-mol glucose per minute. It is a concentrated form of Promozyme with an activity of 600 PUN/ml concentrate.

Example 1

Part A

This example describes a series of enzyme conversions run in a ten gallon gate mixer reactor using Ban (B) and Termamyl (T), and mixtures thereof. The resulting maltodextrins were used in remoistenable adhesives.

The internal dimensions of the tank were 16 inches tall by 16 inches diameter. The gate agitator, made from ½ inch wide by 2 inch deep stainless steel bar stock, had four vertical rakes 10½ inches tall. The outside rakes cleared the inside tank wall by ½ inch; the inside rakes were 3¼ inches from the outside set. Attached to the tank top were four breaker bars, of the same bar stock, located 1¾ and 5¼ inches in from the tank wall. A electric drive, variable from 0 to 60 rpm, powered the agitator. A vent in the tank top provided variable draft forced exhaust. The tank sides and bottom were jacketed for steam heating or water cooling. A ½ inch diameter steam injection port was provided in the side wall 1 inch above the tank bottom. A thermocouple probe was attached to the bottom of one outside breaker bar. In the tank bottom a 2 inch port with a ball valve was provided for product draw off. For these conversions a removable metal plug was inserted into the draw port, flush with the tank bottom, to eliminate the possibility of a portion of the initial dry charge receiving non-uniform moisture, enzyme, or heat.

For each conversion 33 pounds of a commercially dry granular starch was added to the tank. The enzyme charge was diluted with sufficient water to bring the charge to 25 percent moisture on an anhydrous basis. This water/enzyme mix was added to the starch with mixing. The mixture, after addition of the enzyme/water mix, was a blend of dry starch and moist starch aggregates less the one half inch in diameter.

At this point, the agitator is turned off for about 30 minutes to allow the enzyme solution to diffuse through out the starch. The starch, after this rest, was a moist flowable powder.

The mixture was heated, generally by injection of live steam (at 32 psi except where indicated otherwise) into the mixture and/or optionally by heating the tank jacket. Typically, the mass was mixed during heating, but this was not required. Mixing only improved heat transfer.

As the granular starch gelatinized (or the cold-water-insoluble predispersed starch was solubilized), it was converted and the reaction mixture changed from a moist powder to a wet doughy mass and then to a dispersed syrup. These changes occurred as the temperature was increased from 50° C. to 90° C. The temperature at which the onset of liquefaction occurred varied depending on the water content, enzyme activation temperature, and starch type.

In this vented tank, there was some loss of moisture during the full heating cycle. When the injection steam was shut off, the temperature was maintained at the indicated temperature with jacket heating for 30 minutes. The batch was then cooled to less than 50° C. and drawn off. Optionally, the pH was reduced to 3.5 with phosphoric acid and the mixture was held for 30 minutes to deactivate any residual enzyme. The pH was readjusted if required.

Part B

To 43.52 parts of the indicated starch were added a mixture of 6.95 parts water and the indicated amount of Ban and/or Termamyl 120 L. A gate mixer was at 30 rpm while the premix was slowly added in steady stream. Mixing was continued until the starch was uniformly damp. The agitator was shut down and the mixture was heated with live steam and jacketed steam to 82–93° C. (180–200° F.) for 30 minutes. Then 6.94 parts of water were added.

The mixer was restarted and agitation was continued at 30 rpm while the mixture was being heated at 93–99° C. (200–210° F.). When the adhesive product clarified and was smooth, the viscosity and solids were tested. After the test results were recorded, the pH was adjusted to 3.5 with 85% phosphoric acid, and additional acid added, if needed, to end the enzyme activity.

The starch base used, enzyme and amount used, and properties of the an resulting suitable and comparative maltodextrins (solids, D.E., and D.S.) are summarized in Table 1. The three month viscosity stability of the same maltodextrins is reported in Table 2.

TABLE 1

| No. | Starch | Enzyme | Dextrin Solids | D.E. | D.S. |
|---|---|---|---|---|---|
| 1* | 35 WF, Hydroxypropylated Waxy Maize | 0.045 B 0.045 T | 62.2 | 13.7 | 0.16 |
| 2 | 35 WF, Hydroxypropylated Waxy Maize | 0.09 T | 70.9 | 11.0 | 0.16 |
| 3 | 35 WF, Hydroxypropylated Waxy Maize | 0.18 T | 62.8 | 10.6 | 0.16 |
| 4 | Hydroxypropylated Waxy Maize | 0.09 T | 68.9 | 13.2 | 0.09 |
| 5 | Octenylsuccinate Waxy Maize | 0.09 T | 60.2 | 15.2 | 0.02 |
| 6** | 35 WF, Hydroxypropylated Waxy Maize | 0.045 T 0.045 T | 60.0 | 7.4 | 0.16 |
| 7 | 35 WF, Hydroxypropylated Waxy Maize | 0.09 T | 69.0 | 13.6 | 0.16 |
| Comparative Enzyme-Converted Maltodextrins | | | | | |
| 8 | Predispersed Hydroxypropylated Waxy Maize | 0.09 T | 68.5 | 4.1 | 0.09 |
| 9 | Waxy Maize | 0.045 T 0.045 T | Paste | 13.6 | — |
| 10 | Waxy Maize | 0.09 T | 65.0 | 18.7 | — |
| 11 | Cationic Waxy Maize | 0.09 T | 71.0 | 22.2 | 0.04 |
| 12 | Tapioca | 0.09 T | 56.9 | 6.9 | — |
| 13 | Commercial Waxy Maize Maltodextrin | — | 67.0 | 10 | — |
| 14 | Hydroxypropylated Commercial Waxy Maize Maltodextrin | — | 70 | 8.0 | 0.09 |

*For Sample No. 1, the steam pressure was 8 psi.
**For Sample No. 6, the enzyme addition was carried out in two steps.

TABLE 2

| No. | Starch | Maltodextrins Solids | D.E. | D.S. | 3 Month Viscosity (cps) |
|---|---|---|---|---|---|
| Viscosity Aging Characteristics of Suitable Enzyme-Converted Maltodextrins | | | | | |
| 1 | 35 WF, Hydroxypropylated Waxy Maize | 62.2 | 13.7 | 0.16 | clear, flowable >50,000 |
| 2 | 35 WF, Hydroxypropylated Waxy Maize | 70.9 | 11.0 | 0.16 | clear, flowable >50,000 |
| 3 | 35 WF, Hydroxypropylated Waxy Maize | 62.8 | 10.6 | 0.16 | clear, flowable >50,000 |
| 4 | Hydroxypropylated Waxy Maize | 68.9 | 13.2 | 0.09 | clear, flowable >50,000 |
| 5 | Octenylsuccinate Waxy Maize | 60.2 | 15.2 | 0.02 | opaque, flowable paste |
| 6 | 35 WF, Hydroxypropylated Waxy Maize | 60.0 | 7.4 | 0.16 | clear, flowable >50,000 |
| 7 | 35 WF, Hydroxypropylated Waxy Maize | 69.0 | 13.6 | 0.16 | clear, flowable >50,000 |
| Viscosity Aging Characteristics of Comparative-Enzyme Converted Maltodextrins | | | | | |
| 8 | Predispersed WF Hydroxypropylated Waxy Maize | 68.5 | 4.1 | 0.09 | clear paste |
| 9 | Waxy Maize | Paste | 13.6 | — | opaque gel |
| 10 | Waxy Maize | 65.0 | 18.7 | — | clear 2750 |
| 11 | Cationic Waxy Maize* | 71.0 | 22.2 | 0.04 | clear, flowable >50,000 |
| 12 | Tapioca | 56.9 | 6.9 | — | opaque gel |
| 13 | Commercial Waxy Maize Maltodextrin | 67.0 | 10 | — | — |

TABLE 2-continued

| No. | Starch | Maltodextrins Solids | D.E. | D.S. | 3 Month Viscosity (cps) |
|---|---|---|---|---|---|
| 14 | Hydroxypropylated Commercial Waxy Maize Maltodextrin | 70.0 | 8.0 | 0.09 | Clear flowable >50,000 |

Example 2

This example shows the preparation of remoistenable adhesives using the high solids maltodextrins of Example 1.

To the hot maltodextrin syrups from Part A were added 18.29 parts each of ethylene vinyl acetate and polyvinyl acetate together with 0.3 parts of a defoamer. Mixing was continued during cooling. When the temperature was below 60° C. (140° F.), the following ingredients were added: 2.96 of Carbowax 600, 1.98 parts of propylene glycol, 0.20 parts of additional defoamer, and 0.15 parts of a preservative.

The Brookfield viscosity aging and curling of the various maltodextrin syrups used in the above formulation were tested.

A control sample was also prepared using a standard canary waxy maize pyrodextrin which is 100% soluble.

Comparative maltodextrins, prepared by the high solids, single phase process, were also prepared and included in the above adhesive formulation. The comparative maltodextrins were either not chemically derivatized, had too high or too low a degree of substitution, or had too high or too low a dextrose equivalent.

A comparative enzyme-converted maltodextrin, without chemical modification, prepared by a conventional enzyme slurry process, which had a polymodal molecular weight distribution was also used in the adhesive formulation.

The results are shown in Tables 3 and 4.

TABLE 3

Viscosity Aging Characteristics of Adhesives Suitable Enzyme-Converted Maltodextrins

| No. | Starch | Dextrin D.E. | D.S. | Solids | Adhesive Viscosity (cps) Initial | 7 Days | 160 Days |
|---|---|---|---|---|---|---|---|
| Control | Pyrodextrin | 4–5 | — | — | 16,500 | 16,000 | 17,000 |
| 2 | 35 WF Hydroxypropylated Waxy Maize | 11.0 | 0.16 | 70.9 | 10,420 | 9580 | 4150 |
| 3 | 35 WF Hydroxypropylated Waxy Maize | 10.6 | 0.16 | 62.8 | 3720 | 3760 | 13,000 |
| 4 | Hydroxypropylated Waxy Maize | 13.2 | 0.09 | 68.9 | 5900 | 5290 | 5000 |
| 5 | Octenylsuccinate Waxy Maize | 15.2 | 0.02 | 60.2 | 5000 | 6120 | 6850 |
| 6 | 35 WF Hydroxypropylated Waxy Maize | 7.4 | 0.16 | 61.0 | 7500 | 7300 | 54,400 |
| 7 | 35 WF Hydroxypropylated Waxy Maize | 13.6 | 0.16 | 69.0 | 2340 | 3700 | — |
| Comparative - Enzyme Converted Maltodextrins | | | | | | | |
| 8 | Predispersed WF Hydroxypropylated Waxy Maize | 4.1 | 0.09 | 59.4 | 16,500 | 16,680 | >200,000 |
| 9 | Waxy Maize | 13.6 | — | 65.0 | 12,600 | Paste | Paste |
| 10 | Waxy Maize | 18.7 | — | 65.0 | 2170 | 2090 | 2900 |
| 11 | Cationic Waxy Maize* | 22.2 | 0.04 | 66.0 | 5320 | 5020 | 7350 |
| 12 | Tapioca | 6.9 | — | ~60 | Paste | Paste | Paste |
| 13 | Commercial Waxy Maize Maltodextrin | 10 | — | 67.0 | 10,400 | Paste | Paste |
| 14 | Hydroxypropylated Commercial Waxy Maize Maltodextrin | 8.0 | 0.09 | 67.2 | 35,600 | 45,200 | >50,000 @ 90 days |

TABLE 4

Curl Testing of Adhesives Suitable Enzyme-Converted Maltodextrins

| No. | Starch | DE | DS | Adhesive Solids | 50% Relative Humidity (dupl.) | | 12% Relative Humidity (dupl.) | |
|---|---|---|---|---|---|---|---|---|
| Control | Pyro-dextrin | 4–5 | — | 68.4 | 70° | 60° | 127° | 109° |
| 2 | 35 WF Hydroxy-propylated Waxy Maize | 11.0 | 0.16 | 60.0 | 43° | 43° | 91° | 92° |
| 3 | 35 WF Hydroxy-propylated Waxy Maize | 10.6 | 0.16 | 64.2 | 39° | 39° | 73° | 73° |
| 4 | Hydroxy-propylated Waxy Maize | 13.2 | 0.09 | 60.0 | 45° | 46° | 94° | 102° |
| 5 | Octenyl-succinate Waxy Maize | 15.2 | 0.02 | 59.1 | 37° | 53° | 73° | 94° |
| 6 | 35 WF Hydroxy-propylated Waxy Maize | 7.4 | 0.16 | 61.0 | 34° | 34° | 63° | 66° |
| 7 | 35 WF Hydroxy-propylated Waxy Maize | 13.6 | 0.16 | | 31° | 26° | 66° | 58° |
| Comparative - Enzyme Converted Maltodextrins | | | | | | | | |
| 8 | Predispersed WF Hydroxy-propylated Waxy Maize | 4.1 | 0.09 | 59.4 | 65° | 61° | 129° | 125° |
| 9 | Waxy Maize | 13.6 | — | 65.0 | Paste - not run | | | |
| 10 | Waxy Maize | 18.7 | — | 65.0 | 37° | 24° | 58° | 39° |
| 11 | Cationic Waxy Maize* | 22.2 | 0.04 | 66.0 | 21° | 32° | 44° | 56° |
| 12 | Tapioca | 6.9 | — | ~60 | Paste - not run | | | |
| 13 | Commercial Waxy Maize Malto-dextrin | 10 | — | 67.0 | Paste - not run | | | |
| 14 | Hydroxy-propylated Commercial Waxy Maize Malto-dextrin | 8.0 | 0.09 | 67.2 | 33° | 14° | 102° | 59° |

Discussion of Control

The control is a conventional envelope adhesive based on a waxy maize pyrodextrin. It shows an acceptable viscosity and good viscosity stability over time. It shows an undesirably high curl angle at both 50% and 12% relative humidity.

Discussion of Suitable Maltodextrins

Samples 1, 2, 3, and 4 show good initial adhesive viscosity and good viscosity stability over time. Sample 2 shows a minor increase in viscosity due to the higher solids maltodextrin syrup. The use of mixed alpha amylases in Sample 1 shows no significant difference in the resulting adhesive. The use of a higher level of enzyme in Sample 3 causes no significant difference in the resulting adhesive. Sample 4 shows that use of a non-converted starch and a starch having a lower degree of substitution has no significant effect in the resulting adhesive.

Sample 5 illustrates the use of another chemically derivatized starch having a lower degree of substitution. The resulting adhesive is acceptable except for long term viscosity stability, probably due to the low degree of substitution. This shows the use of a non-viscosity stable maltodextrin syrup in these adhesives.

Sample 6 was made with a split addition of the enzyme, ½ into the powder ½ after the mixture's temperature reached 90° C. The resulting syrup is less converted but still shows acceptable adhesive properties.

Sample 7 has higher solids compared to Samples 1 and 3, but the resulting adhesives show no significant differences.

Samples 2, 3, 4, 5, and 7 are examples of the preferred maltodextrins. They show acceptable viscosity and good viscosity stability, as well as reduced curl compared to the control.

Discussion of Comparative Examples

Sample 8 shows the use of a maltodextrin syrup of insufficient conversion, i.e., D.E. less than 5. The resulting adhesive is unacceptable in long term viscosity stability and has unacceptable curl.

Samples 9 and 10 show the use of non-chemically modified maltodextrins with dextrose equivalents in the claimed range. Sample 10, with higher D.E., yields a viscosity stable adhesive with shallow fiber tear. Sample 9, with lower D.E., gives an adhesive which gels in less than seven days.

A highly converted, D.E. 22, modified maltodextrin, Sample 11 gives a viscosity stable, low viscosity adhesive with shallow fiber tear.

Sample 12, an unmodified tapioca, gives an adhesive formula which gels in less than 24 hours.

The adhesive formulated with the commercial waxy maize maltodextrin (Sample 13) which had a D.E. of 10 and a polymodal molecular weight distribution showed an unacceptable viscosity stability. The commercial waxy maize maltodextrin having an original D.E. of 10 was reacted with propylene oxide to a D.S. 0.09, after which it had a D.E. of 8.0. It was then formulated into an adhesive (Sample 14); it showed an unacceptable viscosity stability.

Adhesion Testing

Adhesion testing of the formulated adhesives which did not gel was carried out by determining the percentage of fiber tear on 24 substance weight white wove paper. All adhesives gave 100% fiber tear. The comparative maltodextrins, like the pyrodextrin control, however, gave shallow fiber tear, whereas the adhesives containing suitable maltodextrins (i.e., D.E. between 5 and 19, D.S. >0.01 and <0.50, and polymodal molecular weight distribution) gave deep fiber tears.

Example 3

This example shows the use of a fully converted, hydroxypropylated (PO) waxy maize and a partially converted, unmodified waxy maize, prepared by the high solids, single phase enzyme conversion process in a corrugating adhesive with and without added caustic. These fully solubilized adhesives were compared to a Stein-Hall type control (caustic dispersed carrier starch with suspended raw starches).

At room temperature, the 61% solids converted P.O. waxy maize and the 71% solids converted waxy maize had viscosities of 3000 cps. and >20,000 cps., respectively. When held in a boiling water bath, the materials thinned considerably. At 200° F., the 61% solids converted P.O. waxy maize had a 45 second viscosity as measured in the Stein-Hall cup. To maintain a high solids level and move the adhesive viscosity towards standard levels, the materials were heated prior to being poured in the glue pan.

The 61% solids P.O. waxy maize was evaluated on the corrugator using a standard gap setting of 0.012 in. The adhesive was unable to deliver bonded single face web at speeds above 50 ft./min. When the board was analyzed immediately off the corrugator, there was no evidence of fiber tear. It appeared that the adhesive had not penetrated the paper. Caustic was added to the adhesive to increase alkalinity and improve the adhesives bite into the paper. At 0.5% on the mass of the adhesive, the caustic made a significant difference and the adhesive was run at 175 ft./min.

The 71% partially dispersed converted waxy maize was held at 88° C. (190° F.). Even at that temperature, the viscosity was approximately 2000 cps. To thin the adhesive and add bite, 0.5% caustic was added based on the total mass. At a gap of 0.012 in., the adhesive was able to produce single face web at speeds of 250 ft./min. Board was also produced at a top speed of 450 ft./min.

To compare this adhesive to Stein-Hall adhesives, 250 ft./min. runs were completed at gap settings of 0.008, 0.014, and 0.020 in. The bond strength vs. adhesive pick up were determined using the ICD procedure for pin strength analysis and the ICD enzyme test for pick up. All the experimental adhesives were held between 66 and 93° C. (150° F. and 200° F.). The specifications for the runs are shown below.

| | |
|---|---|
| No. 1 Material: | 63% solids fully dispersed P.O. waxy |
| Speed: | 50 ft./min. |
| Caustic: | none |
| Gap: | 0.012 |
| Pick up: | 1.6 lb/MSF |
| Bond: | 3.1 lb/lineal ft. |
| No. 2 Material: | 63% solids fully dispersed P.O. waxy |
| Speed: | 175 ft./min. |
| Caustic: | 0.5% on total adhesive |
| Gap: | 0.012 |
| Pickup: | 1.6 lb/MSF |
| Bond: | 4.3 lb/lineal ft. |
| No. 3 Material: | 71% solids partially dispersed unmodified waxy |
| Speed: | 250 ft./min. |
| Caustic: | 0.5% on total adhesive |
| Gap: | 0.008 |
| Pick up: | 1.4 lb/MSF |
| Bond: | 10.3 lb/lineal ft. |
| No. 4 Material: | 71% solids partially dispersed unmodified waxy |
| Speed: | 250 ft./min. |
| Caustic: | 0.5% on total adhesive |
| Gap: | 0.014 |
| Pickup: | 5.0 lb/MSF |
| Bond: | 28.0 lb/lineal ft. |
| No. 5 Material: | 71% solids partially dispersed unmodified waxy |
| Speed: | 250 ft./min. |
| Caustic: | 0.5% on total adhesive |
| Gap: | 0.020 |
| Pick up: | 9.9 lb/MSF |
| Bond: | 32.5 lb/lineal ft. |

One major weakness of both adhesives was the final bond strength given the adhesive pick up. An acceptable bond strength is considered to be 50 lb/lineal ft. Even with 9.9 lb/MSF, the better performing 71% solids converted waxy maize was unable to surpass the minimum standard. On the same paper, a Stein-Hall adhesive is capable of achieving a bond strength of 50 lb/lineal ft. using 1.5 lb/MSF. The board produced by the 63% solids converted P.O. waxy maize had virtually no fiber tear. There was a maximum of 25% fiber tear even for the highest pick up of the 71% solids waxy. The partially converted material probably had some higher molecular weight polymer chains which could be the reason for the improved bond strengths.

Example 4

This example describes the preparation of a layflat laminating adhesive.

To a clean, dry tank are added 100 parts of an octenylsuccinate waxy maize (0.02 D.S.) followed by a premix of 31 parts of water and 0.2 parts of Termamyl. Mixing at 20 rpm is carried out while the premix is added in a slow, steady steam. Mixing is continued until the mixture is uniformly damp and then the agitator is shut down. The mixture is heated with live steam and jacketed steam to 93.3° C. (200° F.) for 60 minutes or until liquid forms uniformly around the tank and at the steam lines. The temperature is held at 93.3° C. (200° F.) while mixing at 30 RPM. When the product clarifies and is smooth, the viscosity and solids are tested. After the test results are recorded, then the pH is adjusted to 3.5 with additional acid to end the enzyme activity. The heat is turned off and 10 parts of sodium nitrate are added. The mixture is cooled to below 48.9° C. (120° F.) and 0.30 parts of defoamer, 11 parts of magnesium chloride hexahydrate, 13 parts of calcium chloride, and 0.15 parts of a preservative are added. The resulting high solids maltodextrin should have a DE of about 10 and a total solids content of about 70%.

The Brookfield viscosity is adjusted to 2000–5000 cps by adding water. The adhesive is expected to demonstrate excellent layflat, high solids, good adhesion, and superior stability.

Example 5

This example describes the preparation of a case and carton sealing adhesive.

Using the procedure described in Example 4, a cationic waxy maize starch containing diethylamino groups (0.04 D.S.) is converted using 0.2% Termamyl. The resulting high solids maltodextrin should have a DE of about 18 and a solids content of about 70%. The Brookfield viscosity is adjusted to 500–5000 cps by dilution with water. This adhesive is designed for fast drying, high tack, and excellent adhesion.

Example 6

This example describes the preparation of a grocery bag adhesive.

Using the procedure described in Example 4 a hydroxypropylated waxy maize (D.S. 0.09) was converted using Termamyl. The resulting maltodextrin should have a DE of about 10 and a solids content of about 67%. The maltodextrin is diluted to a 1500–5000 cps Brookfield viscosity. The adhesive should produce faster set, higher solids, stronger adhesion as well as minimal wrinkling compared to a standard bag adhesive.

Example 7

This example describes the preparation of a tubewinding adhesive.

Using the procedure described in Example 4 a hydroxypropylated fluidity waxy maize (35 WF, 0.16 D.S.) was converted using 0.2% Termamyl. The resulting maltodextrin should have a D.E. of about 15 and a solids content of about 68%. The Brookfield viscosity is adjusted to 2000–10,000 cps by dilution with water. This adhesive is designed for superior tack and very fast set speed with minimal puckering and excellent adhesion.

Example 8

This example describes the preparation of an envelope seam adhesive.

Using the procedure described in Example 4, corn starch is converted using 0.2% Termamyl. The resulting maltodextrin should have a D.E. of about 15 and a solids content of about 70%. Fifteen parts of sodium nitrate, 12 parts magnesium chloride hexahydrate, and 8 parts urea, are added and the Brookfield viscosity is adjusted to 200–8000 cps by dilution with water. This adhesive should demonstrate high tabbing resistance due to the elevated solids, excellent rheology for clean machining, good adhesion, and light color which will eliminate discoloration of paper seams.

Example 9

This example describes the preparation of a label wrap adhesive.

Using the procedure described in Example 4, waxy maize starch is enzyme converted using 0.2% Termamyl. The resulting maltodextrin should have a D.E. of about 18 and a solids content of about 70%. Ten parts of sodium nitrate, 15 parts urea, 10 parts magnesium chloride hexahydrate, are added and the Brookfield viscosity is adjusted to 10,000–100,000 cps (which depend on the machinery to be used) using water as the diluent. This adhesive is expected to produce less paper wrinkling, have high tack, good adhesion, and light color.

Example 10

This example describes the use of a fully converted, hydroxypropylated waxy maize starch as cigarette making adhesives in the three bonding applications, i.e., cigarette paper to itself for the side seam, tipping paper to itself, and tipping paper to cigarette paper to mimic the tipping bonds.

A hydroxypropylated waxy maize (0.16 D.S) is converted with 0.2% Termamyl using the procedure of Example 4. The resulting maltodextrin should have a DE of about 15 and a solids content of about 62% (see Table I, Sample 1).

The maltodextrin is diluted with sufficient water to yield an adhesive having a Brookfield viscosity of approximately 3000 cps. The viscosity stability at room temperature and adhesion characteristics are expected to be as good as the adhesives of Example 1.

Example 11

This example shows the use of a maltodextrin-based adhesive as a book casing adhesive where it successfully replaces the animal glue typically used.

Part A—Adhesive Preparation

A fluidity waxy maize (35 WF) was reacted with sufficient propylene oxide to give a D.S. of about 0.16. It was then further converted in the previously described ten gallon gate mixer reactor using 0.2% Termamyl.

For the conversion 33 pounds of the above commercially dry, converted, hydroxy propylated granular starch was added to the tank. The enzyme charge was diluted with sufficient water to bring the charge to 25% moisture on an anhydrous basis. This water/enzyme mix was added to the starch with mixing. The mixture, after addition of the enzyme/water mix, was a blend of dry starch and moist starch aggregates less the one half inch in diameter. At this point, the agitator was turned off for about 30 minutes to allow the water to diffuse throughout the starch. The starch, after this rest, was a moist flowable powder. The mixture was heated by injection of live steam at 32 psi into the mixture. The mass was mixed during heating, but this mixing was not required as mixing only improved heat transfer. As the granular starch gelatinized, it was converted and the reaction mixture changed from a moist powder to a wet doughy mass and then to a dispersed syrup. This change occurred as the temperature was increased from 50° C. to 90° C. (123–195° F.). In this vented tank, there was some loss of moisture during the full heating cycle. When the injection steam was shut off, the temperature was maintained at 90–95° C. (195–204° F.) with jacket heating for 30 minutes. The batch was then cooled to less than 65.6° C. (150° F.) and drawn off. The solids content was about 71% and the DE (which was not recorded) should be about 11.0. The Brookfield viscosity of the 71% solids maltodextrin adhesive was 318,000 cps at room temperature and 12,500 cps at 65.6° C. (150° F.).

Part B—Adhesive Use

The adhesive was coated onto one surface of the substrates as a 1.5 mil film at 65.6° C. (150° F.). The Kraft speed and spin time at 65.6° C. (150° F.) were 20 and 50 seconds, respectively. The animal glue control (67.8% solids) had a Brookfield viscosity at 65.6° C. (150° F.) of 1650 cps and a Kraft speed and open time at 65.6° C. (150° F.) of 25 and 120 seconds, respectively. The adhesion was 25% fiber tear for the maltodextrin adhesive vs. 100% fiber tear for the animal glue when the substrates were canvas/composition board and 100% fiber tear (shallow) when the substrates were glossy overstock/composition board. The fiber tear of the maltodextrin laminated glossy overstock/composition board was somewhat shallow due to the high viscosity of the adhesive.

Part C—Diluted Adhesive Use

The above maltodextrin syrup was diluted to improve the open time. Adhesive A was diluted with water. Adhesive B was diluted with a combination of water and glycerol. The adhesive was coated at 1.5 mil onto the canvas or gloss overstock. The above substrates composition and the properties of the resulting adhesives are shown below.

|  | ADHESIVE A | ADHESIVE B |
|---|---|---|
| Maltodex syrup | 200 g | 200 g |
| Water | 20 g | 10 g |
| Glycerol | — | 20 g |
| Solids | 68 % | 68 % |
| Brookfield Viscosity at Room Temperature (cps) | 32,800 | 28,200 |
| Kraft Speed (sec.) | 20 | 40 |
| Open Time (sec.) | 40 | 130 |
| Adhesion | 100 % | 100 % |

-continued

|  | ADHESIVE A | ADHESIVE B |
| --- | --- | --- |
| Canvas/Composition Board | 100 % | 100 % |
| Glossy Cover Stock/ Composition Board | 100 % | 100 % |

The results show that the adhesive containing the water and glycerol had an open time as good as the animal glue control (130 sec. vs. 120 sec. for the control) but that the Kraft speed increased (40 sec. vs. 25 sec for the control). The adhesion was as good as the animal glue control for both substrates. Adhesive A had a 40 sec. open time due to its high solids content and high viscosity; however, the open time can be increased by diluting the adhesive with water which will not have a detrimental effect on the other properties.

Now that the preferred embodiments of the invention have been described in detail, various modifications and improvements thereon will become readily apparent to those skilled in the art. Accordingly, the spirit and scope of the present invention are to be limited only by the appended claims and not by the following specification.

What is claimed:

1. A remoistenable adhesive which consists essentially of:
   a) at least about 50% by weight of a maltodextrin syrup having a solids content between about 60 to about 80% by weight and a water content of about 40 to about 20% by weight, which is prepared from a converted or a non-converted, chemically derivatized starch formed by heat and/or acid-conversion, oxidation, phosphorylation, etherification, esterification, crosslinking, and enzyme modification and having an amylose content of 40% or less; which maltodextrin has (i) substituents in an amount sufficient to provide a degree of substitution of greater than about 0.01 and less than about 0.50; (ii) a reducing sugar content of between about 5 and about 19 dextrose equivalent; and (iii) a polymodal molecular weight distribution having one peak between about 630 to about 1600 daltons and at least one other peak between about 1600 and about 2,500,000 daltons;
   b) 0 to about 50% by weight of water; and
   c) an effective amount, based on the weight of the maltodextrin syrup in the remoistenable adhesive, of a preservative, a humectant, a defoamer, a plasticizer, a rheology modifier, and/or a peptizing salt.

2. The adhesive of claim 1, wherein the starch is a waxy starch, a corn starch, a tapioca starch, a wheat starch, a rice starch, or a potato starch; wherein the maltodextrin contains ether and/or ester substituent groups; wherein the solids content of the maltodextrin syrup is about 60% to about 75% and the water content of the maltodextrin syrup is about 40% to about 25%; and wherein the amount of the maltodextrin syrup in the adhesive is about 70% to less than 100%.

3. The adhesive of claim 2, wherein the starch is the waxy starch; wherein the ether and/or ester substituent groups are non-ionic, anionic, and/or cationic groups; wherein the degree of substitution is between about 0.05 and less than about 0.17; wherein the other peaks are between about 1600 and about 160,000 daltons; wherein the solids content of the maltodextrin syrup is about 65 to about 75% and the water content of the maltodextrin syrup is about 35 to about 25%; and wherein the amount of the maltodextrin syrup in the adhesive is about 70% to about 90%.

4. The adhesive of claim 3, wherein the starch is the waxy maize starch; wherein the ether substituents are hydroxypropyl, 3-(trimethyl ammonium)-2-hydroxypropyl, or N,N-diethylaminoethyl, groups; and wherein the ester groups are succinate, octenylsuccinate, acetate or phosphate groups.

5. A remoistenable adhesive which consists essentially of (a) a maltodextrin dextrin syrup which is prepared by a process comprising the steps of (i) reacting an unconverted or a converted granular starch having an amylose content of 40% or less with a sufficient amount of a chemical derivatizing reagent to produce a granular, derivatized starch having a degree of substitution of greater than about 0.01 and less than about 0.50, (ii) adding to the granular, derivatized starch water and an effective amount of an enzyme which cleaves the 1→4, or 1→6, or both the 1→4 and 1→6 linkages of the starch, or a mixture of the enzymes, the water being added to the starch and the enzyme(s) in an amount sufficient to produce a powdered mixture without a visible free water phase, (iii) activating the enzyme(s), and (iv) allowing the enzyme(s) to hydrolyze and liquefy the starch to a maltodextrin syrup and the maltodextrin has a solids content of about 60 to about 80% and a water content of about 40 to about 20% by weight, a dextrose equivalent of about 5 to about 19, and (b) an effective amount, based on the weight of the maltodextrin syrup in the remoistenable adhesive, of a preservative, a humectant, a defoamer, a plasticizer, and/or a peptizing salt.

6. The adhesive of claim 5, further comprising step (v) of inactivating the enzyme(s) and wherein the enzyme is an alpha amylase, a beta amylase, an amyloglucosidase, an isoamylase, or a pullulanase.

7. The adhesive of claim 6, wherein the starch is a waxy starch, a corn starch, a tapioca starch, a wheat starch, a rice starch, or a potato starch; wherein the derivatized starch contains non-ionic, anionic, or cationic, ether and/or ester substituent groups; wherein the degree of substitution is between about 0.05 and about 0.17; wherein the maltodextrin has the dextrose equivalent between about 10 and about 17; wherein the solids content of the maltodextrin syrup is about 65 to about 75% and the water content of the maltodextrin syrup is about 35 to about 25%; and wherein the enzyme is the alpha amylase or the mixture of the alpha amylase and the beta amylase.

8. The adhesive of claim 7, wherein the starch is the waxy starch; wherein the ether groups are hydroxypropyl, 3-(trimethyl ammonium)-2-hydroxypropyl groups, or N,N-diethylaminoethyl groups; and wherein the ester groups are succinate, octenylsuccinate, acetate or phosphate.

9. A non-remoistenable adhesive which consists essentially of:
   a) at least about 50% by weight of a maltodextrin syrup having a polymodal molecular weight distribution and a solids content between about 60 to about 80% by weight and a water content of about 40% to about 20% by weight and which is prepared from a converted or a non-converted starch and which maltodextrin has a reducing sugar content of between about 5 and about 19 dextrose equivalent;
   b) 0 to about 50% by weight of water; and
   c) an effective amount, based on the weight of the maltodextrin syrup in the non-remoistenable adhesive, of a preservative, a humectant, a defoamer, a plasticizer, and/or a peptizing salt.

10. The adhesive of claim 9, wherein the starch is a waxy starch, a corn starch, a tapioca starch, a wheat starch, a rice starch, a potato starch, or a high amylose starch; and wherein the solids content of the maltodextrin syrup is about 60 to about 75% and the water content of the maltodextrin syrup is about 40 to about 25%.

11. The adhesive of claim 10, wherein the starch is the waxy maize starch; wherein the solids content of the maltodextrin syrup is about 65 to about 75% and the water content of the maltodextrin syrup is about 35 to about 25%; and wherein the amount of the maltodextrin syrup in the adhesive is about 70%.

12. The adhesive of claim 9, wherein the starch is a waxy starch, a corn starch, a tapioca starch, a wheat starch, a rice starch, or a high amylose starch; and wherein the starch contains non-ionic, anionic, or cationic ether and/or ester substituent groups.

13. The adhesive of claim 12, wherein the starch is the waxy maize starch; wherein the ether groups are hydroxypropyl, 3-(trimethyl ammonium)-2-hydroxypropyl or N,N-diethylaminoethyl groups; and wherein the ester groups are succinate, octenylsuccinate, acetate, or phosphate.

14. A non-remoistenable adhesive which consist essentially of (a) a maltodextrin dextrin syrup which is prepared by a process comprising the steps of (i) adding to a granular, converted or unconverted starch water and an effective amount of an enzyme which cleaves the 1Δ4, or 1→6, or both the 1→4 and 1→6 linkages of the starch, or a mixture of the enzymes, the water being added to the starch and the enzyme(s) in an amount sufficient to produce a powdered mixture without a visible free water phase, (ii) activating the enzyme(s), and (iii) allowing the enzyme(s) to hydrolyze and liquefy the starch to a maltodextrin syrup having, a solids content of about 60 to about 80% and a water content of about 40 to about 20%, with the maltodextrin having a DE of about 5 to about 19; and (b) an effective amount, based on the weight of the maltodextrin syrup in the non-remoistenable adhesive, of a preservative, a humectant, a defoamer, a plasticizer, and/or a peptizing salt.

15. The adhesive of claim 14, wherein the starch is a waxy starch, a corn starch, a tapioca starch, a wheat starch, a rice starch, a potato starch, or a high amylose starch; wherein the starch is derivatized and contains non-ionic, anionic, or cationic ether and/or ester substituent groups and the degree of substitution is between about 0.05 and about 0.17; wherein the maltodextrin has the dextrose equivalent between about 10 and about 17; wherein the solids content of the maltodextrin syrup is about 60 to about 75% and the water content of the maltodextrin syrup is about 40 to about 25%; and wherein the enzyme is an alpha amylase, a beta amylase, an amyloglucosidase, an isoamylase, or a pullulanase.

16. The adhesive of claim 15, wherein the starch is the waxy maize starch; wherein the ether groups are hydroxyalkyl, 3-(trimethylammonium)-2-hydroxypropyl or N,N-diethylaminoethyl groups; wherein the ester groups are succinate, octenylsuccinate, acetate, or phosphate, wherein the enzyme is the alpha amylase or the mixture of the alpha amylase and the beta amylase and wherein the solids content of the maltodextrin syrup is about 65 to about 75% and the water content of the maltodextrin syrup is about 35 to about 25%.

* * * * *